US00PP14419P29

(12) United States Plant Patent
Heims

(10) Patent No.: US PP14,419 P2
(45) Date of Patent: Dec. 23, 2003

(54) LOBELIA PLANT NAMED 'CRANBERRY CRUSH'

(50) Latin Name: ***Lobelia sessilifolia*×*Lobelia siphilitica***
Varietal Denomination: Cranberry Crush

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 10/345,688

(22) Filed: Jan. 15, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Klarquist Sparkman, LLP

(57) ABSTRACT

A new and distinct hybrid of Lobelia plant characterized by a dwarf habit, and large deep red purple flowers.

1 Drawing Sheet

Botanical classification: Lobelia hybrid (*Lobelia sessilifolia*×*Lobelia siphilitica*).
Variety denomination: 'Cranberry Crush'.

BACKGROUND OF THE INVENTION

The present invention relates to a new and distinct hybrid of Lobelia and given the cultivar name 'Cranberry Crush' because of the flower color and the short stature of the plant. Lobelia is in the family Lobeliaceae. This new hybrid originated as a cross between *Lobelia sessilifolia* (seed parent), an unpatented plant, and *Lobelia siphilitica* dwarf (pollen parent), an unpatented plant.

This plant is unique due to its combination of dwarf habit and cranberry crimson flower color. It is characterized by the following:

1. Dwarf habit.
2. Numerous large, deep cranberry crimson flowers held over the foliage.
3. Strong, short flowering stems that don't fall over.
4. Long blooming, as no seed is produced.

The new variety has been reproduced only by asexual propagation (cuttings and micropropagation). Each of the progeny exhibits identical characteristics to the original plant. Asexual propagtion by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old Lobelia 'Cranberry Crush' growing in the trial fields in August in Canby, Oreg.

DETAILED PLANT DESCRIPTION

The following is a detailed description of the new Lobelia hybrid based on observations of a two-year-old specimen grown in the field in Canby, Oreg. The color descriptions are all based on The Royal Horticultural Society Colour Chart.

Botanical name: Lobelia hybrid (*Lobelia sessilifolia*× *Lobelia siphiltica*).
Cultivar name: 'Cranberry Crush'.

Plant:
- *Type.*—Herbaceous perennial.
- *Hardiness.*—USDA Zones 4 to 9.
- *Size.*—32 cm. wide and 36 to 61 cm. tall.
- *Form.*—Basal clump.

Leaf:
- *Type.*—Simple.
- *Shape.*—Oblanceolate.
- *Arrangement.*—Rosette to alternate up flowering stem.
- *Length.*—5 to 12 cm.
- *Width.*—2 to 3.5 cm.
- *Margins.*—Irregularly and coarsely serrate.
- *Apex.*—Acute to acuminate.
- *Base.*—Attenuate.
- *Texture.*—Soft leather.
- *Aspect.*—Matte.
- *Vestiture.*—Puberulent.
- *Venation.*—Pinnate.
- *Petiole length.*—Sessile.
- *Color.*—Topside — Green 137A. Bottom — Closest to Yellow Green 147B.

Inflorescence:
- *Type.*—Terminal raceme.
- *Peduncle.*—Height: 40 to 80 cm. Diameter: 0.4 to 0.7 cm. Vestiture: Hispid. Color: Yellow Green 144A.
- *Pedicel.*—Length: 0.5 cm. Texture: Hispid. Color: Yellow Green 144B.
- *Flower number.*—50 per raceme with secondary flowers later in the leaf axils.

Flower bud:
- *Size.*—3.9 cm. deep and 0.7 cm. wide.
- *Shape.*—Oblong. Tube-like on bottom ⅔ then constricted and top ovoid with an acute tip.
- *Color.*—Red Purple 71B.
- *Texture.*—Setose.

Flower:
- *Type.*—Zygomorphic.
- *Shape.*—Bilabiate.
- *Size.*—3 cm. deep and 3.5 cm. wide.

*Corolla.*—Slit to the base on the upper side between the two upper lobes, upper lobes recurve slightly and are 2 cm long and 0.3 cm wide, lower three lobes spreading and 1.9 cm long and 0.6 cm wide. Tube is 2.5 cm long and 0.7 cm wide.

*Texture.*—Satiny.

*Color.*—Deep red purple. Closest to Red Purple 71A but a deeper color.

*Calyx.*—5 deeply cut acuminate lobes, linear lanceolate, parted to corolla base, cupped back. Margins ciliate.

*Calyx lobe size.*—2.7 cm deep and 0.25 cm wide at base.

*Calyx color.*—Yellow Green 144A. Tips and edges maroon, Greyed Purple 187B.

*Pistil.*—3.4 cm. long, Greyed Purple 186C.

*Stamen number.*—5 in a column around the stigma, Red Purple 71A.

*Filament length.*—2.7 cm.

*Anther size before dehiscing.*—0.5 cm.

*Pollen color.*—Creamy yellow, Yellow 10D.

*Bloom period.*—July and August in Canby, Oreg.

*Fragrance.*—None.

Fruit:

*Number.*—50 per raceme.

*Shape.*—Ovoid.

*Size.*—2 mm wide and 4 mm long.

*Type.*—Dehiscent capsule.

*Color.*—Tan, Grey Brown 199D.

Seed: None produced.

*Fertility.*—Sterile.

Pest resistance: No observed pest resistance.

Disease: None observed on plant grown under commercial conditions in Canby, Oreg.

COMPARISONS TO SIMILAR LOBELIA

Compared to Lobelia 'Ruby Slippers', an unpatented plant, this new cultivated variety is much shorter and as such the flowers don't fall over. The new cultivar also blooms earlier.

Compared to Lobelia 'Royal Purple', an unpatented plant, this new cultivated variety is shorter and has flowers of deep cranberry crimson rather than a deep purple.

Compared to Loblia 'Grape Knee-Hi' (U.S. Plant Pat. No. 13,264), this new cultivar has deep cranberry crimson flowers rather than deep purple. Both cultivars share the trait of having their flowering stems stay upright.

Compared to its seed parent, *Lobelia sessilifolia*, the new variety has darker, redder flowers, and is much shorter.

Compared to its pollen parent, *Lobelia siphilitica* dwarf, the new variety is slightly taller and has a more open inflorescence and much darker flowers.

I claim:

1. A new and distinct hybrid of Lobelia plant substantially as shown and described, characterized by a dwarf habit and deep cranberry crimson flowers.

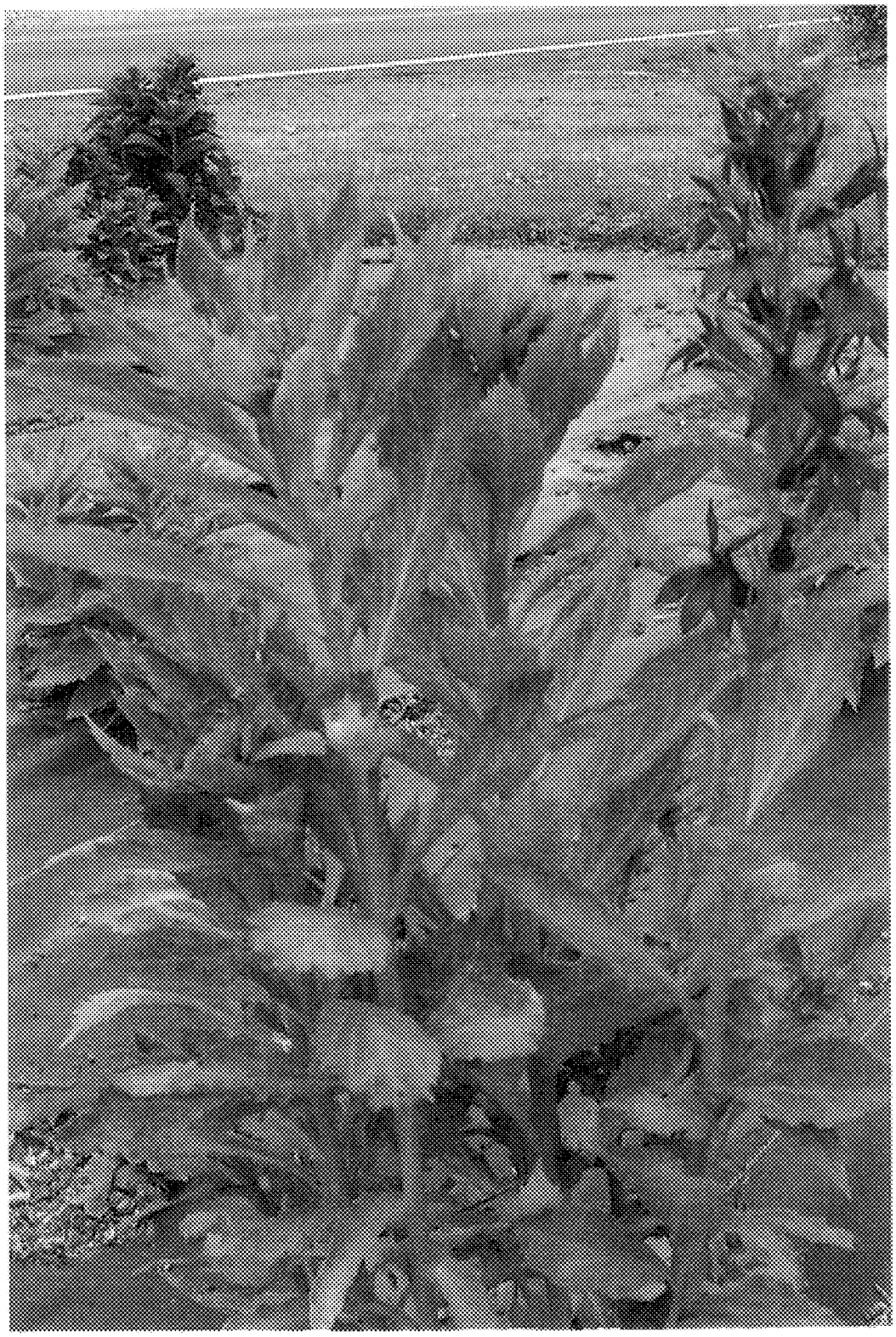

* * * * *